US011306364B2

(12) United States Patent
Yan et al.

(10) Patent No.: US 11,306,364 B2
(45) Date of Patent: Apr. 19, 2022

(54) TERT PROMOTER MUTATIONS IN GLIOMAS AND A SUBSET OF TUMORS

(71) Applicants: Duke University, Durham, NC (US); The Johns Hopkins University, Baltimore, MD (US)

(72) Inventors: Hai Yan, Durham, NC (US); Bert Vogelstein, Baltimore, MD (US); Nickolas Papadopoulos, Towson, MD (US); Kenneth W. Kinzler, Baltimore, MD (US); Yuchen Jiao, Columbia, MD (US); Chetan Bettegowda, Lutherville, MD (US); Darell D. Bigner, Mebane, NC (US); Zachary J. Reitman, Durham, NC (US); Patrick J. Killela, Durham, NC (US)

(73) Assignees: Duke University, Durham, NC (US); The Johns Hopkins University, Baltimore, MD (US)

( * ) Notice: Subject to any disclaimer, the term of this patent is extended or adjusted under 35 U.S.C. 154(b) by 122 days.

(21) Appl. No.: 16/928,164

(22) Filed: Jul. 14, 2020

(65) Prior Publication Data

US 2020/0399708 A1     Dec. 24, 2020

Related U.S. Application Data

(62) Division of application No. 14/765,692, filed as application No. PCT/US2014/016906 on Feb. 18, 2014, now Pat. No. 10,711,310.

(60) Provisional application No. 61/772,249, filed on Mar. 4, 2013, provisional application No. 61/766,857, filed on Feb. 20, 2013, provisional application No. 61/765,909, filed on Feb. 18, 2012.

(51) Int. Cl.
*C12Q 1/6886* (2018.01)
*C07H 21/04* (2006.01)

(52) U.S. Cl.
CPC ...... *C12Q 1/6886* (2013.01); *C12Q 2600/112* (2013.01); *C12Q 2600/156* (2013.01)

(58) Field of Classification Search
None
See application file for complete search history.

(56) References Cited

U.S. PATENT DOCUMENTS

| 7,879,609 B2 | 2/2011 | Morin et al. |
| 2006/0088850 A1 | 4/2006 | Tapscott et al. |

FOREIGN PATENT DOCUMENTS

| CN | 1282422 A | 1/2001 |
| JP | 2005304497 A | 11/2005 |
| WO | 2004016813 A2 | 2/2004 |

OTHER PUBLICATIONS

Feb. 2, 20216—(EP) Notice of Opposition—Patent No. 3360979.
Nault et al., "High frequency of telomerase reverse-transcriptase promoter somatic mutations in hepatocellular carcinoma and preneoplastic lesions," Nature Communications, 4:2218, (2013).
Nault et al., "High frequency of telomerase reverse-transcriptase promoter somatic mutations in hepatocellular carcinoma and preneoplastic lesions," Nature Communications, Supplementary Material (2013).
Killela et al., "TERT promoter mutations occur frequently in gliomas and a subset of tumors derived from cells with low rates of self-renewal," PNAS, vol. 110, No. 15, pp. 6021-6026 (2013).
Killela et al., "TERT promoter mutations occur frequently in gliomas and a subset of tumors derived from cells with low rates of self-renewal," PNAS, vol. 110, No. 15, Supporting Information (2013).
Killela et al., "TERT promoter mutations occur frequently in gliomas and a subset of tumors derived from cells with low rates of self-renewal," PNAS, vol. 110, No. 15, Supporting Data (2013).
Huang et al. "Highly Recurrent TERT Promoter Mutations in Human Melanoma" Science, vol. 339, Supplementary Fig. S1 (2013).
Scott et al., "Mutations of the TERT promoter are common in basal cell carcinoma and squamous cell carcinoma," Modern Pathology, vol. 27, pp. 516-526 (2014).
Liu et al., "Highly prevalent TERT promoter mutations in aggressive thyroid cancers," Endocrine-Related Cancer, vol. 20, No. 4, pp. 603-610 (2013).
Kim et al., "Specific Association of Human Telomerase Activity with Immortal Cells and Cancer," Science, vol. 266, pp. 2011-2015 (1994).
Horn et al., "TERT Promoter Mutations in Familial and Sporadic Melanoma," Science, vol. 339, Supplementary Materials (2013).
Japanese Office Action issued in related Japanese Application No. 2015-558198, dated Jul. 21, 2016.
Huang et al. "Highly Recurrent TERT Promoter Mutations in Human Melanoma" Science, vol. 339, Feb. 22, 2013, pp. 957-959.
Horn et al., "TERT Promoter Mutatiosn in Familial and Sporadic Melanoma," Science, vol. 339, Feb. 22, 2013, pp. 959-961.

(Continued)

*Primary Examiner* — Sarae L Bausch
(74) *Attorney, Agent, or Firm* — Banner & Witcoff, Ltd.

(57) ABSTRACT

We surveyed 1,230 tumors of 60 different types and found that tumors could be divided into types with low (<15%) and high (≥15%) frequencies of TERT promoter mutations. The nine TERT-high tumor types almost always originated in tissues with relatively low rates of self renewal, including melanomas, liposarcomas, hepatocellular carcinomas, urothelial carcinomas, squamous cell carcinomas of the tongue, medulloblastomas, and subtypes of gliomas (including 83% of primary glioblastoma, the most common brain tumor type). TERT and ATRX mutations were mutually exclusive, suggesting that these two genetic mechanisms confer equivalent selective growth advantages. In addition to their implications for understanding the relationship between telomeres and tumorigenesis, TERT mutations provide a biomarker for the early detection of urinary tract and liver tumors and aid in the classification and prognostication of brain tumors.

39 Claims, 3 Drawing Sheets

(56) References Cited

OTHER PUBLICATIONS

Di Stefano et al., "Association between glioma susceptibility loci and tumour pathology defines specific molecular etiologies," Neuro-Oncology 15(5):1542-547, 2013.
Extended European Search Report issued in related European Application No. 18164632.4, dated Jul. 11, 2018.
Park et al., "886 HTERT Promoter Gene Polymorphism and the Risk of Hepatocellular Carcinoma (HCC) in Patients with Chronic Hepatitis B," Journal of Hepatology, vol. 52, Apr. 1, 2010, p. S345.
Yao, "Dynamic alteration of telomerase expression and its diagnostic significance in liver or periperal blood for hepatocellular carcinoma," World Journal of Gastroenterology, vol. 12, No. 31, Jan. 1, 2006, p. 4966.
Nagao et al., "Telomerase reverse transcriptase mRNA expression and telomerase activity in hepatocellular carcinoma," Journal of Gastroenterology, vol. 34, No. 1, Jan. 22, 1999, pp. 83-87.
Hartmann et al., "Telomerase gene mutations are associated with cirrhosis formation," Hepatology, vol. 53, No. 5, May 1, 2011, pp. 1608-1617.
Carpentier et al. "Association of telomerase gene hTERT polymorphism and malignant gliomas" J. Neurononcolo. (2007) 84:249-253.
Jun. 12, 2019—(EP) Summons to attend Oral Proceedings—App. 18164632.4.
Kheirollahi et al. "Alterations of telomere length in human brain tumors" Medical Oncology, vol. 28, No. 3, 2011, pp. 864-870.
Yan et al. "IDH1 and IDH2 mutations in gliomas" The New England Journal of Medicine, vol. 360, No. 8, 2009, pp. 765-773.
Killela et al. "TERT promoter mutations occur frequently in gliomas and a subset of tumors derived from cells with low rates of self-renewal" PNAS, vol. 110, No. 15, Mar. 25, 2013, pp. 6021-6026.
Arita et al. "Upregulating mutations in the TERT promoter commonly occur in adult malignant gliomas and are strongly associated with total 1p19q loss" Acta Neuropathologica, vol. 126, No. 2, Jun. 14, 2013, pp. 267-276.
Fearon et al. "Genetic and Epigenetic Alterations in Cancer" In: "Abeloff's Clinical Oncology: Fifth Edition" Oct. 22, 2013, pp. 188-203.e.1.
Jiao et al. "Telomerase reverse transcriptase mutations in plasma DNA in patients with hepatocellular carcinoma or cirrhosis: Prevalence and risk factors" Hepatology Communications, Jun. 2018, vol. 2, No. 6, pp. 718-731.
Gillet et al. "The clinical relevance of cancer cell lines" Journal of the National Cancer Institute, vol. 105, No. 7, Apr. 3, 2013, pp. 452-458.
Lacroix "Persistent use of "false" cell lines" International Journal of Cancer, vol. 122, No. 1, Jan. 1, 2008, pp. 1-4.
Berglind et al. "Analysis of p53 mutation status in human cancer cell lines: a paradigm for cell line cross-contamination" Cancer Biology & Therapy, vol. 7, No. 5, May 2008, pp. 699-708.
Hirshfield et al. "Germline Mutations and Polymorphisms in the Origins of Cancers in women" Journal of Oncology, vol. 2010, Jan. 1, 2010, pp. 1-11.
Soussi "Handbook of p53 Mutation in Cell Lines" Jul. 1, 2007, Retrieved from the Internet: URL:http://p53.free.fr/Database/Cancer_cell_lines/cell_lines_1.0.pdf.
Dec. 19, 2019—(JP) Notification of Third-Party Submission of Information—App 2017-194782.
Dec. 17, 2019—(JP) Third-Party Submission of Information—App 2017-194782.
Huang et al. "Highly Recurrent TERT Promoter Mutations in Human Melanoma" Science, vol. 339, Feb. 22, 2013, pp. 957-959; Supplementary Materials 1 (www.sciencemag.org/cgi/content/full/science.1229259/DC1 <https://protect-us.mimecast.com/s/sdX7C0RAgMi2Qm7wTwbXBz>) and Table S1 of Supplementary Materials (https://science.sciencemag.org/highwire/filestream/594302/field_highwire_adjunct_files/0/1229259TableS1.xl <https://protect-us.mimecast.com/s/MtRsCwpnjxULkyq3cAGLme>sx).
Websiteof ATCC [5637 (ATCC HTB-9)](https://www.atcc.org/products/all/HTB-9 <https://protect-us.mimecast.com/s/HigBCxkoGyiJDx7otNi1LG>.aspx)], Mar. 1974.
Website of ATCC [Daoy (ATCC HTB-186)](https://www.atcc.org/products/all/HTB-186.aspx <https://protect-us.mimecast.com/s/4P2_CkR65ginA5KzU9nFjG>), 1985.
Website of ATCC [Hep G2 [HEPG2] (ATCC HB-8065](https://www.atcc.org/products/all/HB-8065.aspx <https://protect-us.mimecast.com/s/zd6JCIY8O0somXVNC1DcjL>), 1983.
Website of JCRB Cell Bank [ONS-76](https://cellbank.nibiohn.go.jp/~cellbank/en/search_res_det.cgi?RNO=IFO50355 <https://protect-us.mimecast.com/s/72qJCmZ7wkU58WgNiDIwrM>), 2005-2015.
Website of ExPASy [RT-112](https://web.expasy.org/cellosaurus/CVCL_1670 <https://protect-us.mimecast.com/s/Xw9JCn5GZIUGgmPNipUEcC>), Apr. 4, 2012.
Website of ATCC [SNU-387 (ATCC CRL-2237)](https://www.atcc.org/products/all/CRL-2237.aspx <https://protect-us.mimecast.com/s/QYsQCo2AYmCX5vg3C7Cj5c>), 1990.
Website of ATCC [SNU-423 (ATCC CRL-2238)](https://www.atcc.org/products/all/CRL-2238.aspx <https://protect-us.mimecast.com/s/bbZVCpY9gnszqAV3UxMZ2o>), 1990.
Website of ATCC [SNU-475 (ATCC CRL-2236)](https://www.atcc.org/products/all/CRL-2236.aspx <https://protect-us.mimecast.com/s/1YL4CqxAjoHOnXEjfp3Me4>), 1990.
Website of JCRB Cell Bank [T24](https://cellbank.nibiohn.go.jp/~cellbank/cgi-bin/search_res_det.cgi?ID=491), 2005-2015.
Website of KAC Co., Ltd [U-87MG](https://www.saibou.jp/service/kensaku/detail.php?catalogno=EC89081402-F0 <https://protect-us.mimecast.com/s/KwSrCv2mgwCWqAYzigEdTa>), 2020.
Dec. 12, 2019—(JP) Notice of Opposition—JP Patent No. 6574385—Eng. Transl.

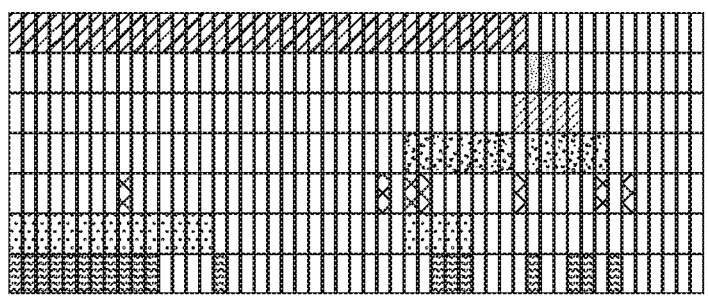
FIG. 2A  PRIMARY GLIOBLASTOMAS
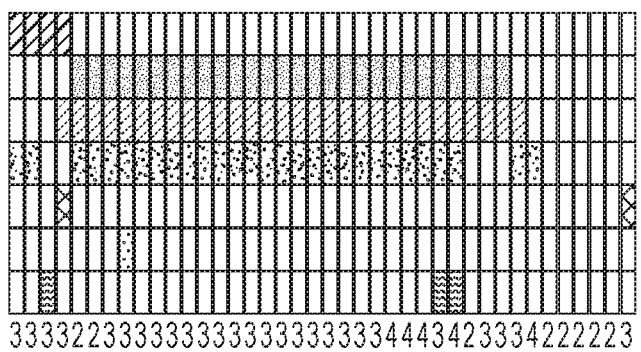
FIG. 2B  ASTROCYTOMAS
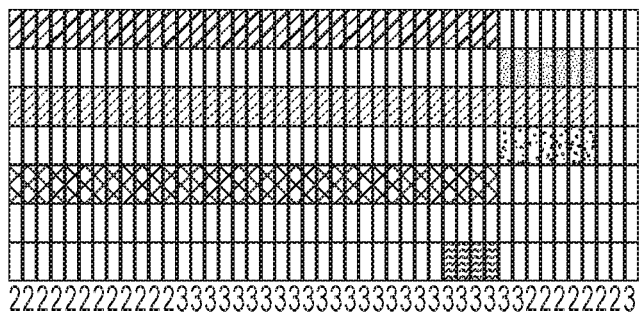
FIG. 2C  OLIGODENDROGLIOMAS
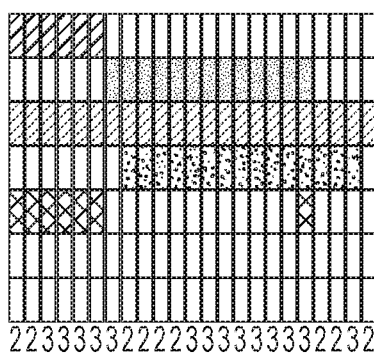
FIG. 2D  OLIGOASTROCYTOMAS
TERT
ATRX
IDH1/2
TP53
Chr1p/19q LOH
EGFR AMPLIFICATION
CDKN2A/B DELETION

TERT PROMOTER MUTATIONS IN GLIOMAS AND A SUBSET OF TUMORS

TECHNICAL FIELD OF THE INVENTION

This invention is related to the area of mutation detection. In particular, it relates to mutations in non-coding regions of the human genome.

BACKGROUND OF THE INVENTION

Telomeres are nucleoprotein complexes at the ends of eukaryotic chromosomes that are required for chromosomal integrity. Several hundred nucleotides of telomere repeats cap each chromosomal end, and in the absence of telomerase activity, telomeres shorten with each cell division (1). Eventually, uncapped telomeres trigger cell death or senescence. Cancer cells seem to divide ad infinitum and therefore, require some telomere maintenance mechanism to avoid this fate. Because telomerase activity is generally higher in cancer cells than normal cells, it was originally believed that telomerase was somehow activated in cancer cells (2-6). However, it was subsequently realized that telomerase was only inactive in terminally differentiated cells and that normal stem cells in self-renewing tissues retained telomerase activity (1, 7-9). Because normal stem cells must replicate throughout the long lifetimes of mammals (which can be more than a century in humans), it is clear that such cells must also retain telomerase activity. Because normal stem cells are thought to be the progenitors of cancers, there would be no need to specifically activate telomerase in cancer cells; the enzyme was already active in the precursors, just as were the hundreds of other enzymes and proteins normally required for cell proliferation.

This view was challenged by the discovery of another mechanism for maintaining telomere length i.e., alternative lengthening of telomeres (ALT) (10-12). ALT occurs in the absence of telomerase activity and seems to be dependent on homologous recombination. It occurs in a particularly high fraction of certain tumor types, such as sarcomas, pancreatic neuroendocrine tumors, and brain tumors, but rarely in most common tumor types, such as those tumor types of the colon, breast, lung, prostate, or pancreas (13). Why would cancer cells need ALT if telomerase activity was already constitutively active in their precursors? This question was highlighted by the discovery that many ALT cancers harbor mutations in alpha thalassemia/mental retardation syndrome X-linked (ATRX) or death-domain associated protein (DAXX), genes encoding proteins that interact with each other at telomeres (10, 11). Presumably, the absence of functional ATRX/DAXX complexes permits the homologous recombination resulting in ALT. At minimum, these data were compatible with the ideas that there could be a selective advantage for genetic alterations that results in telomere maintenance and that telomerase is not indefinitely activated in all normal stem cell precursors of cancers.

Another challenge to the idea that genetic alterations were not required for telomerase activation in cancer was raised by the finding that mutations of the telomerase reverse transcriptase (TERT) promoter occurred in ~70% of melanomas and in a small number of tumor cell lines derived from various tissue types (14, 15). Importantly, only 5 of 110 cell lines derived from lung, stomach, ovary, uterus, or prostate cancers harbored TERT promoter mutations, whereas 19 mutations were found among 37 cell lines derived from various other tumor types. This situation is analogous to the situation for ALT, which is infrequently observed in common epithelial cancers but is observed more regularly in tumors derived from nonepithelial cells, particularly sarcomas and brain tumors (13).

There is a continuing need in the art for biomarkers that help detect, monitor, and characterize tumors, as well as that help predict the effects of tumors on patients.

SUMMARY OF THE INVENTION

According to one aspect of the invention a method is provided for testing a nucleic acid sample of a human. A nucleic acid sample of a human is tested and the presence of a somatic mutation in a promoter of a telomerase reverse transcriptase (TERT) gene is determined. The nucleic acid is from a cancer selected from the group consisting of: a sarcoma, a hepatocellular carcinoma, urinary tract cancer, a head and neck cancer, a medulloblastoma, a glioma, an astrocytoma, an oligodenderoglioma, and an oligoastrocytoma.

Another aspect of the invention is a modified nucleic acid probe. It comprises at least 18 nucleotides of a human TERT promoter. The 18 nucleotides include C228A or C229A.

Another aspect of the invention is a modified nucleic acid primer. It comprises at least 18 nucleotides of a human TERT promoter. The 18 nucleotides include C228A or C229A.

These and other embodiments which will be apparent to those of skill in the art upon reading the specification provide the art with new tools for characterizing tumors and managing care of cancer patients.

BRIEF DESCRIPTION OF THE DRAWINGS

FIGS. 2A-2D. Mutations of selected genes in glioma subtypes. (FIG. 2A) Distribution of TERT mutations and other genetic events in 51 primary GBMs. (FIG. 2B) Distribution of TERT mutations and other genetic events among 40 astrocytomas, including grades II-III astrocytomas and grade IV secondary GBMs. (FIG. 2C) Distribution of TERT mutations and other genetic events among 45 oligodendrogliomas. (FIG. 2D) Distribution of TERT mutations and other genetic evens among 24 oligoastrocytomas. World Health Organization tumor grade is indicated under each column. Blank box denotes WT status in tumors.

DETAILED DESCRIPTION OF THE INVENTION

Figure 1:
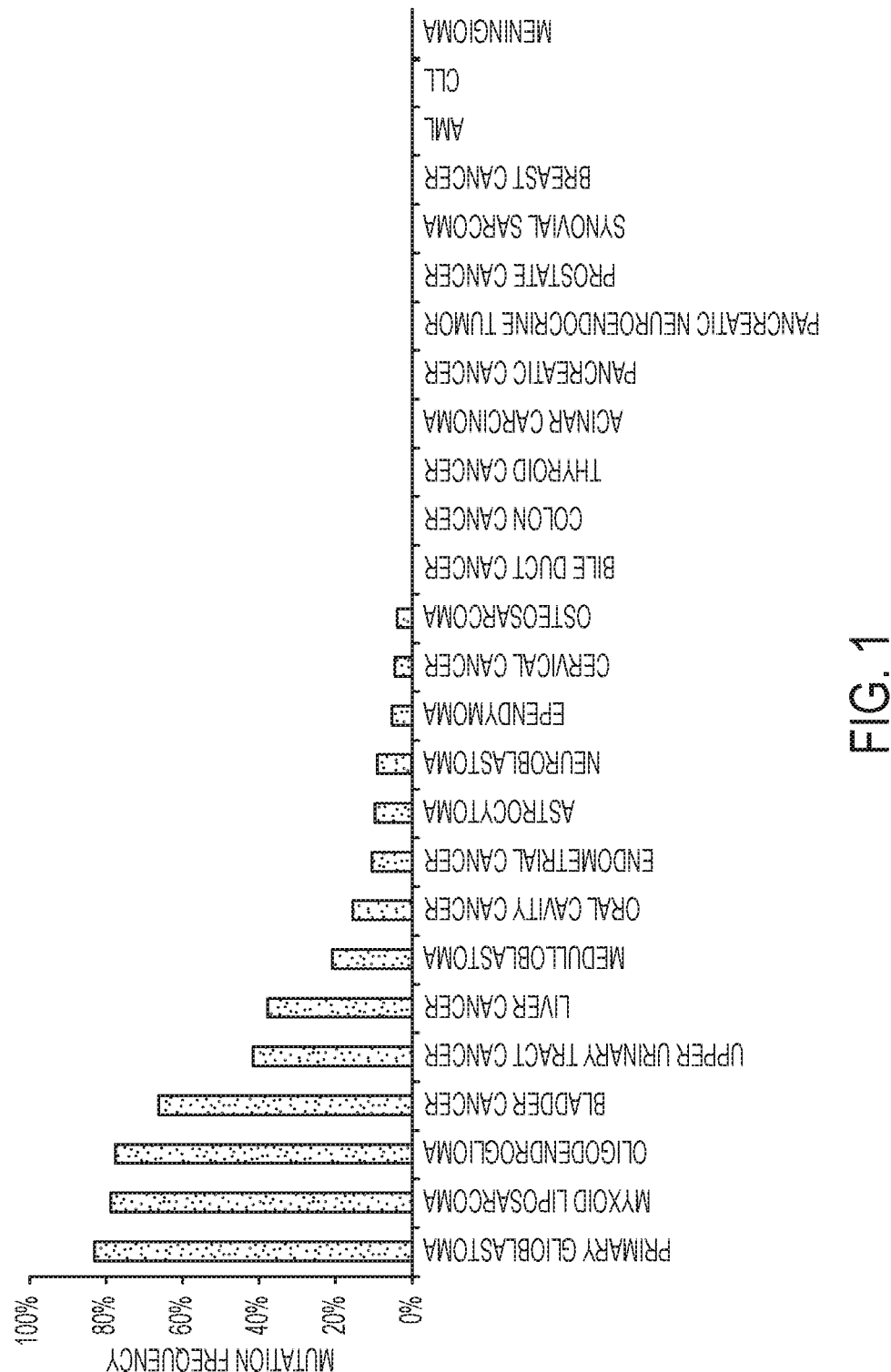
FIG. 1. Frequency of TERT promoter mutations; 15 or more tumors were analyzed in 26 tumor types. Gliomas are divided into primary GBM, astrocytoma (including astrocytoma grades II and III, as well as secondary GBM), and oligodendroglioma.

The inventors have developed assays that are useful for characterizing tumors. The assays involve biomarkers which are nucleic acid mutations, typically a single nucleotide mutation in a non-coding region of chromosome 5. The mutations are located in the promoter region of telomerase reverse transcriptase (TERT), at particular sites, particularly at 1,295,228; 1,295,229; and 1,295,250 (hg19). Such mutations have the effect of increasing expression of telomerase reverse transcriptase.

Biological samples which can be used in the present methods include, but are not limited to, samples containing tissues, cells, and/or biological fluids isolated from a subject. Examples of biological samples include, but are not limited to, tissues, cells, biopsies, blood, lymph, serum, plasma, urine, saliva, mucus and tears. Biological samples may be tissue samples (such as a biopsy). Biological samples may be obtained directly from a subject (e.g., by blood or tissue sampling) or from a third party (e.g., received from an intermediary, such as a healthcare provider or lab technician). Nucleic acids may be isolated and/or purified prior to assaying. Nucleic acids are not obtained from cell lines grown in culture for numerous generations, because such cell lines develop mutations during the immortalization and culturing processes that do not reflect in vivo tumorigenesis.

Nucleic acids can be assayed using techniques such as amplification and hybridization and nucleic acid sequencing. Primers and probes can be mutation specific. Alternatively, primers can be generic and amplify a region that includes that potentially mutated region, whether mutant or not. A second technique can then be used to identify the mutation.

Mutations can be identified as somatic by comparing the tumor DNA to DNA from a normal tissue of the human patient. Normal or control DNA can be obtained from a tissue that is not involved in the cancer. The presence of a mutation in the tumor DNA but not in the control DNA indicates that the mutation is somatic, i.e., it is not inherited.

Probes and primers which are used in the method can be have any usable chemistry, so long as they have suitable base sequence and function in the assay to specifically hybridize and/or prime synthesis. Particular probes and primers may optionally have chemistries that are not naturally occurring, such as modified or alternative backbone chemistry, or additional moieties such as labels or enzymes, or additional base sequences that are not found in the TERT gene promoter region adjacent to the TERT gene promoter-hybridizing sequences of the probes or primers. The modified or alternative chemistries may enhance stability of a nucleotide or enhance hybridization, for example, relative to naturally occurring nucleic acids. Probes and/or primers may also be bound to solid supports, such as arrays or beads.

Typically probes and primers are sufficiently long to achieve specific hybridization to the desired target sequence without spurious hybridization to other non-target sequences. Typically the size of such nucleic acids is at least 12, at least 14, at least 16, at least 18, at least 20, at least 22, at least 24, at least 26, at least 28, or at least 30 nucleotides and less than 200, less than 150, less than 125, less than 100, less than 75, less than 50, or less than 40 nucleotides.

The high prevalence of the TERT promoter biomarkers in certain cancers make them useful for detection of cancers at an early stage and for following patients for evidence of progression or recurrence once they have been diagnosed. Such detection and monitoring can be done in samples such as plasma, cerebrospinal fluid, and urine, and other body fluids or tissues. Tumors that are the source of the analyte nucleic acids may be primary tumors or metastases.

Once a TERT promoter mutation is identified in one of the test nucleic acids, treatment or prophylaxis can be recommended and/or administered. The presence or absence of TERT promoter mutation may characterize the subtype of tumor or cell type source of the tumor into a group of more similar tumors, providing refinement to the recommended or prescribed treatment or monitoring plan. Suitable treatments may involve watchful waiting, chemotherapy, radiotherapy, biological therapy, surgery, or other suitable management. Inhibitory agents such as antibodies and inhibitory RNA molecules may also be used, once a TERT promoter mutation is identified.

We formulated a hypothesis about the mechanisms responsible for telomerase activity in cancers. We suggest that there are two ways to maintain telomere lengths as cells divide: (i) through epigenetic regulation of telomerase activity, which occurs in stem cells of tissues that are rapidly renewing, and (ii) through somatic mutations that maintain telomere lengths, such as mutations in the TERT promoter or mutations in DAXX or ATRX. Those cancers that originate in tissues that are constantly self-renewing, such as cancers of the epithelia of the gastrointestinal tract and skin or bone marrow, would be unlikely to harbor telomere-maintaining mutations, because telomerase is already epigenetically activated in their precursor cells. In contrast, tumors arising from cells that are not constantly self-renewing, such as neurons, glial cells, fibroblasts, hepatocytes, islet cells, and pancreatic ductal epithelial cells, might frequently harbor such mutations. A corollary of this hypothesis is that tumor types exhibiting high frequencies of ALT would also exhibit high frequencies of TERT mutations, and these mutations would be distributed in a mutually exclusive fashion. To test these hypotheses as well as answer other questions related to the role of TERT promoter mutations in various cancer types, we determined the prevalence of TERT promoter mutations in a large number of tumors.

The results described below, as well as the results published in refs. 14 and 15, provide evidence that supports one of the hypotheses raised in the Introduction and refutes others. The first of these hypotheses was that TERT mutations would only be observed in tumors derived from tissues that are not constantly self-renewing under normal circumstances. This hypothesis was supported in part: the vast majority of TERT promoter mutations occurred in tumors derived from tissues that do not continually self-renew. The TERT-H tumor types include only melanomas, certain subtypes of glioma, medulloblastomas, squamous cell cancers of the tongue, liposarcomas, HCCs, and urinary tract cancers. The normal transitional cells of the urinary tract have very low proliferative indices (0.64%±0.52%), much lower than indices of gastrointestinal tract, bone marrow, or skin (38). Normal hepatocytes also do not turnover often (39), and glial cells are thought to have limited capacity for self-renewal (40).

Two other observations also support the hypothesis. Pediatric primary GBMs rarely contained TERT mutations (11%), whereas adult primary GBMs frequently did (83%). Pediatric GBMs are presumably derived from cells that are still dividing at the time of tumor initiation, and therefore, there is no selective advantage conferred by activating telomerase through a genetic mutation. Adult GBMs, in contrast, are presumably derived from postmitotic cells, and they should require telomerase activation. Similarly, medulloblastomas are embryonal tumors that typically arise from precursor cells with high self-renewal rates that do not usually persist in adults. This finding is consistent with our observation that the mean age of medulloblastoma patients with TERT mutations was considerably older than the mean age of medulloblastoma patients without TERT mutations.

There are, however, exceptions that belie the hypothesis that TERT mutations occur only in non-self-renewing tissues. The epithelium that lines the tongue constantly selfrenews, but many squamous carcinomas of the tongue harbored TERT mutations. Additionally, the squamous epithelia of the tongue certainly would not be expected to self-renew less than other squamous epithelia of the oral cavity, but the latter rarely harbored TERT mutations. This finding may suggest that squamous carcinomas of the tongue originate from a different cell of origin than other oral cavity squamous carcinomas. Conversely, only a subset of the tumor types derived from non-self-renewing tissues was TERT-H. For example, the TERT-H tumors included myxoid liposarcomas but not synovial sarcomas. Moreover, cells of the pancreas (the islets of Langerhans and the ductal epithelial cells) rarely renew, but pancreatic tumors of all types (pancreatic neuroendocrine tumors, acinar carcinomas, and pancreatic ductal adenocarcinomas) were all TERT-L. The most that we can conclude at present is that non-self-renewing cell types are the major sources of TERT-H tumors but that non-self-renewal is only one of the factors that determines whether tumor cells with TERT promoter mutations will have a selective growth advantage over adjoining cells.

The first corollary to the hypothesis raised above was that tumor types that displayed ALT would be those types that harbored TERT promoter mutations. This corollary is soundly refuted by these data, at least in general terms. Although tumor types of the CNS and liposarcomas had high frequencies of ALT as well as high frequencies of TERT promoter mutations, these tumor types were the exceptions rather than the rule. For example, pancreatic neuroendocrine tumors have very high frequencies of ALT but no evidence of TERT mutations. Conversely, bladder cancers frequently have TERT mutations but never have ALT (13). Additionally, even among gliomas, pediatric GBMs have high frequencies of ALT and low frequencies of TERT mutations, whereas adult GBMs have the reverse pattern.

The second corollary was that the selective advantage afforded by TERT mutation would be equivalent to the advantage afforded by ATRX mutation (conferring ALT). This hypothesis was most effectively tested in gliomas, in which both ATRX coding and TERT promoter mutations were common. There was a striking mutual exclusivity with respect to ATRX and TERT mutations (P<0.0001), lending strong support to this idea.

These results also raise many unanswered questions. In some tumor types, such as gliomas, we can imagine that all tumors have genetically activated telomere maintenance programs through mutations in either TERT or ATRX. However, in other tumor types with frequent ATRX mutations, such as pancreatic neuroendocrine tumors, what is responsible for activating telomerase in the fraction of cases not exhibiting ALT if it is not a mutation in the TERT promoter? Similarly, what is responsible for activating telomerase in those tumors derived from non-self-renewing cell types in which neither ALT nor TERT mutations is frequently observed, such as synovial sarcomas or osteosarcomas? Also, there are occasional individual tumors among the TERT-L types that have TERT promoter mutations (e.g., cervical cancers, ovarian cancers, and in ref. 15, lung cancers). What distinguishes these occasional cancers from others of the same histopathologic subtype? Whole-genome sequencing studies, rather than those studies limited to the exome, might provide answers to these questions.

The results recorded here have practical as well as basic scientific implications. Two-thirds of bladder cancers had TERT promoter mutations, making it the most commonly mutated gene yet identified in invasive urothelial carcinoma of the bladder. Given the persistently high mortality rate despite multimodality treatment in this group of patients, these mutations represent ideal urinary biomarkers to detect bladder cancers at an early stage and to follow patients for evidence of progression or recurrence once they have been diagnosed (41). Similarly, the high prevalence of TERT promoter mutations in HCCs and glioma subtypes provides excellent candidate biomarkers for early detection (HCC) or monitoring (HCC in the plasma and gliomas in the cerebrospinal fluid) (42, 43).

Figure 3:
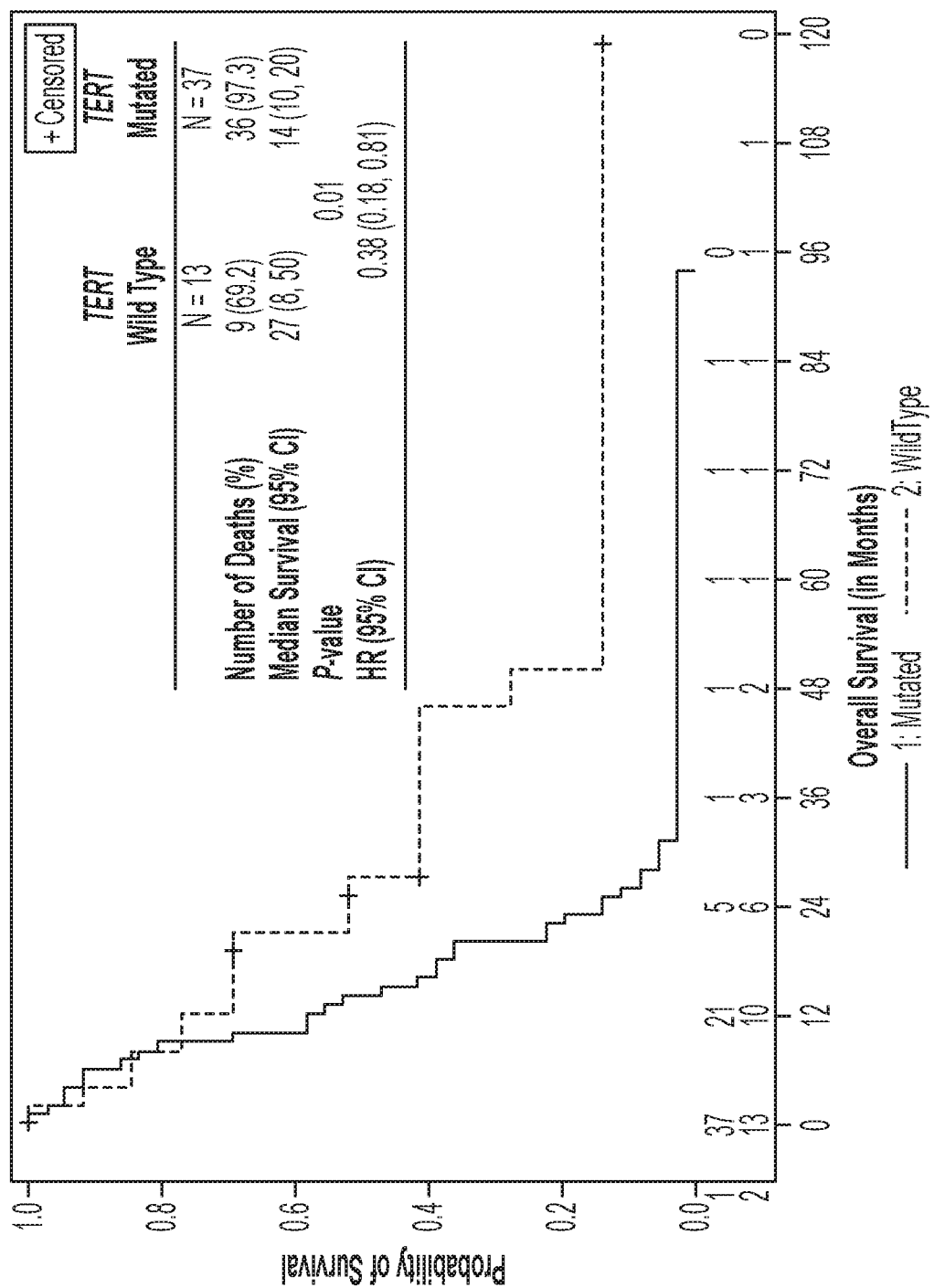
FIG. 3. Survival of primary GBM patients with TERT promoter-mutated tumors. Kaplan-Meier analysis of 50 primary GBM patients stratified by TERT promoter mutational status. Patients with TERT promoter WT tumors (n=13) survived longer than patients with TERT promoter-mutated tumors (n=37); median survival was 27 mo among the patients with TERT promoter WT tumors compared with 14 mo among patients with TERT promoter-mutated tumors. The estimated hazard ratio was 0.38 (95% confidence interval=0.18, 0.81; P=0.01, log rank test).

Another practical implication involves diagnostics. We conjecture that tumors with TERT promoter or ATRX mutations are derived from different precursor cells and that either type of precursor cell is different from those types that are the precursors of tumors without such mutations. This distinction could aid classification of the tumors in clinically meaningful ways. For example, FIG. 2 outline the major genetic alterations occurring in the three most common types of gliomas. On the basis of the data in FIG. 2 A-C, we speculate that oligodendrogliomas that lack TERT mutations but contain ATRX mutations may behave more like astrocytomas than oligodendrogliomas and vice versa. Similarly, the primary GBMs without TERT mutations (15% of the total) may behave more like advanced progressive astrocytomas, which generally lack TERT mutations. This possibility is supported by the observation that those primary GBM patients without TERT mutations had a longer survival, on average, than other primary GBM patients (FIG. 3).

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1—Methods

All clinical information and tissue were obtained with consent and Institutional Review Board approval from the various institutions donating material to this study, and they were obtained in accordance with the Health Insurance Portability and Accountability Act. Tissue sections were reviewed by board-certified pathologists to ensure that ≥50% of the cells used for DNA purification were neoplastic and confirm histopathological diagnosis. Oligonucleotides with the sequences 5'-M13-GGCCGATTCGACCTCTCT-3' (SEQ ID NO: 1) and 5'-AGCACCTCGCGGGTAGTGG-3' (SEQ ID NO: 2), where M13 is a universal sequencing priming site with sequence 5'-tgtaaaacgacggccagt-3' (SEQ ID NO: 3), were used to PCR-amplify the proximal TERT promoter containing C228 and C250 (chr5: 1,295,228; chr5: 1,295,250, respectively; hg19) for Sanger sequencing using standard methods (44). Primary GBM copy number data as well as ALT status were derived from the data published in refs. 37, 45, and 46, and OTX2 copy number expression was derived from the data published in ref. 27. Brain tumor patients were treated at the Tisch Brain Tumor Center at Duke. For the purposes of this study, secondary GBM designates a GBM that was resected >1 year after a prior diagnosis of a lower-grade glioma (grades I-III), and all other GBMs were considered to be primary GBMs. Pediatric GBM samples were defined as those samples occurring before 21 years of age.

Example 2

We attempted to evaluate at least 20 individual specimens of common tumor types and fewer specimens of rare tumor types, depending on availability of specimens in our laboratories. In those tumor types in which our pilot studies showed a significant number of mutations, additional tumors were evaluated. Melanomas and tumors of the lung, stomach, and esophagus were excluded, because they had already been adequately evaluated in the seminal papers cited (14, 15). When primary tumors rather than cell lines were used, we ensured that the fraction of neoplastic cells was >50% through histopathologic examination of frozen sections of the tissue blocks used for DNA purification. In those cases in which the neoplastic content was <50%, we microdissected the lesions to enrich the neoplastic content to >50%. Primers were designed to amplify the region containing the two TERT mutations that were previously described—C228T and C250T—corresponding to the positions 124 and 146 bp, respectively, upstream of the TERT ATG start site (14, 15). The PCR fragments were then purified and analyzed by conventional Sanger sequencing.

In all, we evaluated TERT promoter mutations in 1,230 tumor specimens and identified 231 mutations (18.8%) (Table 1). C228T and C250T mutations accounted for 77.5% and 20.8% of the alterations, respectively. Additionally, we detected four mutations that had not been observed previously: three C228A mutations and one C229A mutation. All four of these mutations as well as a representative subset of the C228T and C250T mutations (n=59) were somatic, as evidenced by their absence in normal tissues of the patients containing the mutations in their tumors.

TABLE 1

Frequency of TERT promoter mutations

| Tumor type* | No. tumors | No. tumors mutated (%) |
|---|---|---|
| Chondrosarcoma | 2 | 1 (50) |
| Dysembryoplastic neuroepithelial tumor | 3 | 1 (33.3) |
| Endometrial cancer | 19 | 2 (10.5) |
| Ependymoma | 36 | 1 (2.7) |
| Fibrosarcoma | 3 | 1 (33.3) |
| Glioma† | 223 | 114 (51.1) |
| Hepatocellular carcinoma | 61 | 27 (44.2) |
| Medulloblastoma | 91 | 19 (20.8) |
| Myxofibrosarcoma | 10 | 1 (10.0) |
| Myxoid liposarcoma | 24 | 19 (79.1) |
| Neuroblastoma | 22 | 2 (9) |
| Osteosarcoma | 23 | 1 (4.3) |
| Ovarian, clear cell carcinoma | 12 | 2 (16.6) |
| Ovarian, low grade serous | 8 | 1 (12.5) |
| Solitary fibrous tumor (SFT) | 10 | 2 (20.0) |
| Squamous cell carcinoma of head and neck | 70 | 12 (17.1) |
| Squamous cell carcinoma of the cervix | 22 | 1 (4.5) |
| Squamous cell carcinoma of the skin | 5 | 1 (20) |
| Urothelial carcinoma of bladder | 21 | 14 (66.6) |
| Urothelial carcinoma of upper urinary epithelium | 19 | 9 (47.3) |

*No mutations were found in acute myeloid leukemia (n = 48), alveolar rhabdomyosarcoma (n = 7), atypical lipomatous tumor (n = 10), breast carcinoma (n = 88), cholangiosarcoma (n = 28), central/conventional chondrosarcoma (n = 9), chronic lympoid leukemia (n = 15), chronic myeloid leukemia (n = 6), colorectal adenocarcinoma (n = 22), embryonal rhabdomyosarcoma (n = 8), esthesioneuroblastoma (n = 11), extraskeletal myxoid chondrosarcoma (n = 3), fibrolammellar carcinoma of the liver (n = 12), gall bladder carcinoma (n = 10), gastrointestinal stromal tumor (n = 9), hepatoblastoma (n = 3), leiomyosarcoma (n = 3), conventional lipoma (n = 8), low grade fibromyxoid sarcoma (n = 9), malignant peripheral nerve sheath tumor (n = 3), medullary thyroid carcinoma (n = 24), meningioma (n = 20), mesothelioma (n = 4), pancreatic acinar carcinoma (n = 25), pancreatic ductal adenocarcinoma (n = 24), pancreatic neuroendocrine tumor (n = 68), prostate carcinoma (n = 34), spinal ependymoma (n = 9), synovial sarcoma (n = 16), or undifferentiated pleomorphic soft tissue sarcoma (n = 10) samples.
†Glioma comprises 11 subtypes; see Table 2.

TABLE 2

TERT mutations in glioma subtypes

| Glioma subtype | WHO grade | No. of tumors studied | No. of tumors with TERT promoter mutation | Tumors with TERT mutation (%) |
|---|---|---|---|---|
| Primary GBM, adult | IV | 78 | 65 | 83 |
| Primary GBM, pediatric | IV | 19 | 2 | 11 |
| Astrocytoma | II | 8 | 0 | 0 |
| Astrocytoma | III | 27 | 4 | 15 |
| Astrocytoma | IV | 5 | 0 | 0 |
| Oligodendroglioma | II | 19 | 12 | 63 |
| Oligodendroglioma | III | 26 | 23 | 88 |
| Oligoastrocytoma | II | 9 | 2 | 22 |
| Oligoastrocytoma | III | 15 | 4 | 27 |

The 1,230 tumors represented 60 tumor types. In 26 of these tumor types, at least 15 individual tumors were evaluated (comprising a total of 1,043 individual tumors) (FIG. 1). In the remaining tumor types, only a small number of samples (2-12) was available, in part because these tumor types are generally uncommon in Western populations (Table 1). Among the tumor types in which at least 15 individual tumors were available for study, a clear distinction could be made. Eighteen of these tumor types had only occasional TERT promoter mutations (zero to three mutations, comprising 0-15% of the tumors of each type) (FIG. 1). We classified these tumor types as TERT-low (TERT-L), because they had a low frequency of TERT promoter mutations. Eight other tumor types were classified as TERT-high (TERT-H) because of their relatively high prevalence of TERT promoter mutations (16-83% of the tumors of each type).

The TERT-L tumor types included some of the most prevalent cancers, including epithelial tumors of the breast, prostate, thyroid, pancreas, gall bladder, uterus, and colon (as well as tumors of the lung, stomach, and esophagus based on prior studies) (14, 15) and leukemias. In fact, no TERT mutations were identified in any specimen of 30 tumor types that we studied, comprising a total of 546 tumors (Table 1). Some nonepithelial cancers, such as synovial sarcomas, chordomas, neuroblastomas, osteosarcomas, and ependymomas, were also TERT-L.

Eight TERT-H tumor types were identified (in addition to the previously described melanomas) (14, 15). These tumors included tumors of the CNS, transitional cell carcinomas of the urinary tract, hepatocellular carcinomas, myxoid liposarcomas, and
oral cavity carcinomas. Although only a small number of TERT-H tumors (other than melanomas) were examined in previous studies (15), mutations in gliomas, hepatocellular, and oral cavity carcinomas were detected, which would be expected on the basis of the high frequency of mutation in these tumors types (Table 1).

Example 3

Sarcomas.

One of the highest frequencies of TERT promoter mutation was found in myxoid liposarcoma (19 of 24 tumors, 79% with mutation). Myxoid liposarcomas account for more than one-third of all liposarcomas and ~10% of all adult soft tissue sarcomas (16). Patients are relatively young, with a peak age range between 30 and 50 y. At the genetic level, the most characteristic change is a t(12; 16) (q13; p11) chromosomal translocation that results in the fusion of the FUS and DDIT3 genes (16, 17). The cellular origin of these tumors is unknown, but preadipocytic progenitor cells and mesenchymal stem cells have been implicated (18); after embryogenesis, the mitotic activity of these cells is thought to be low. Other sarcomas, also thought to originate from mesenchymal cells that do not self-renew in the absence of damage, were not TERT-H (Table 1). These sarcomas included synovial sarcomas (0% of 16 tumors) and osteosarcomas (4.3% of 23 tumors). Of note, myxoid liposarcomas have been previously shown to have a relatively high prevalence of ALT (24% of 38 tumors) (13, 19). The data, in aggregate, are compatible with the idea that myxoid liposarcomas almost always genetically activate telomere maintenance genes through either TERT promoter mutations or ALT.

Hepatocellular Carcinomas.

Hepatocellular carcinomas (HCCs) are the third leading cause of cancer mortality worldwide, and their incidence is increasing in the United States (20). Most HCCs in the United States are associated with Hepatitis B or C Virus infection, whereas others are associated with alcoholic cirrhosis; 44% of HCC samples that we evaluated harbored TERT promoter mutations (27/61). This finding makes TERT the most commonly mutated gene yet observed in this tumor type (21, 22). The mutations seemed to occur relatively early in tumorigenesis, because they were observed in 39% of stage I well-differentiated HCCs (Table S1). TERT mutations were observed in virally associated tumors as well as cases without any underlying liver disease at similar frequencies (Table S1). There was also no difference in the prevalence of TERT promoter mutations with respect to sex, age, or ethnicity (Table S1). ALT has been observed in 7% of 121 HCCs studied previously (13).

Urinary Tract Cancers.

Urothelial carcinoma of the bladder is the fourth most common type of cancer in American males. In 2013, over 73,000 patients will be diagnosed with bladder cancer leading to approximately 15,000 deaths in the US alone (23). Two-thirds of the 21 urothelial carcinomas of the bladder that we studied harbored TERT promoter mutations. We were also able to evaluate 19 urothelial carcinomas of the upper urinary tract, a much less common anatomic site for this histopathologic subtype of tumor. Nine of nineteen upper urinary tract urothelial carcinomas harbored TERT mutations. TERT mutations are, therefore, the most frequently mutated genes yet identified in urothelial carcinoma of either the bladder or upper urinary tract (24). The prevalence of ALT in bladder cancers is very low (1% of 188 cancers) (13).

Head and Neck Cancers.

Head and neck cancers are almost always squamous cell carcinomas and can occur throughout the oral cavity lining (mucous membranes of the cheek, hard and soft palate, tongue, supraglottis, etc.). It is the sixth most common cancer in the world, and 50,000 cases occurred in the United States in 2012. We identified TERT promoter mutations in 17% of 70 oral cavity cancers that we evaluated. However, the anatomic distribution of the cases with TERT promoter mutations was striking: 11 of 12 cancers with TERT promoter mutations were in the oral tongue, although only 23 of 70 total cases originated in the oral tongue (P<0.0001, Fisher exact probability test, two-tailed) (Table S2). The basis for this extraordinary selectivity is curious given the shared characteristics of the squamous epithelium lining the tongue and other parts of the head and neck, including the oral cavity. Moreover, we evaluated 22 squamous cell carcinomas of another site (the cervix) and found only one TERT mutation (4.5%) (Table 1). Most cervical squamous cell carcinomas and a subset of head and neck squamous cell carcinomas are caused by human papillomavirus, which can activate telomerase by expressing E6 and E7 viral oncogenes (25). These findings raise the possibility that human papillomavirus infection and TERT mutation may be alternative mechanisms to activate telomerase among squamous cell carcinomas. We were unable to test correlations between TERT promoter mutations and HPV status or other clinical parameters because of the small number of patients with available data (Table S2). There have been no ALT cases identified among 70 head and neck cancers, including 41 oral cavity cancers (13).

Medulloblastomas.

Medulloblastoma is the most common malignant brain tumor of childhood (26). TERT mutations occurred in 21% of 91 medulloblastomas that we evaluated. As with the oral cavity cancers, TERT mutations were not distributed randomly among the medulloblastoma patients. Although medulloblastomas are usually diagnosed at a young age, those medulloblastomas with TERT mutations were diagnosed at a considerably older age (median=6 vs. 16 y, P=0.0012, t test assuming unequal variances, two-tailed) (FIG. S1A). This observation has important implications for understanding the basis for the selectivity of the tumor types harboring TERT promoter mutations (Discussion); 45 of 90 patients had been assessed previously for orthodenticle homeobox 2 (OTX2) gene amplification and expression, and alterations in this transcription factor are known to correlate with clinically distinct molecular subtypes of medulloblastoma (27). OTX2 expression was >100-fold higher in medulloblastoma patients without TERT promoter mutations than in those patients with TERT promoter mutations (note the log scale in FIG. S1B). The high levels of OTX2 expression were usually the result of OTX2 gene amplification (FIG. S1C). The association of TERT promoter mutations with an older age at diagnosis and a lack of OTX2 overexpression raises the possibility that TERT mutations occur in a specific clinical and molecular subtype of medulloblastoma. The most likely molecular subtype of medulloblastoma that may be enriched for TERT mutations is the noninfant sonic hedgehog subtype, which is characterized by an older age at diagnosis and lower expression of OTX2 (28, 29). Larger studies will be needed to make this association more definitive. ALT has been observed in 7% of 55 medulloblastomas studied previously (13).

Gliomas.

Gliomas are the most common CNS tumor type and accounted for >14,000 deaths in the United States last year (30). Histopathological and clinical criteria established by the World Health Organization are used to characterize these tumors into several subtypes (30). We considered the four main subtypes individually (Table S3).

Primary Glioblastoma.

These primary glioblastomas (GBMs) are the most common malignant brain tumors in adults, accounting for ~17% of all intracranial tumors, and they confer the worst survival (median of ~15 mo) (31). These high-grade (grade IV) tumors have no detectable precursor lesions and have been referred to as de novo tumors. The prevalence of TERT promoter mutations was remarkably high in GBMs of adults (83% of 78 tumors) (Table S3). This prevalence is higher than the prevalence of any other genetic mutation in this tumor type (32). These findings provide a molecular mechanism responsible for the high levels of TERT mRNA and telomerase activity observed in GBMs (33).

For 51 of 78 primary GBM tumors, data on other common genetic alterations as well as clinical data were available (FIG. 2A). Interestingly, EGFR amplification, a classic molecular feature of primary GBM, exclusively occurred in tumors with TERT mutations (P=0.0006, Fisher exact probability test, two-tailed). Conversely, no association was identified between TERT mutation and either TP53 mutation or CDKN2A deletion. Importantly, the frequency of TERT promoter mutations was considerably less in primary GBMs of pediatric patients (11% of 19 tumors) than adult patients (Discussion) (Table S3). ALT was observed in 11% of 105 adult GBM and 44% of pediatric GBM (i.e., the reverse of the pattern observed for TERT promoter mutations) (13). Primary GBM patients without TERT mutations survived considerably longer, on average, than patients with such mutations (median=27 vs. 14 mo, P=0.01 by the log rank test) (FIG. S3).

Astrocytomas.

Infiltrative astrocytic tumors frequently progress, with recurrent lesions often of higher grade than the original lesions excised at surgery. They are most often grade II or III but can progress to grade IV (at which point they are often termed secondary GBMs). Astrocytomas of any stage rarely contained TERT promoter mutations (10% of 40 total samples) (Table S3). Instead, they more frequently contained isocitrate dehydrogenase 1 (IDH1) or isocitrate dehydrogenase 2 (IDH2) mutations (75% of 40 tumors), ATRX mutations (70% of 40 tumors), and TP53 mutations (73% of 40 tumors) (FIG. 2B). ALT has been observed in 63% of 57 astrocytomas, consistent with the high prevalence of ATRX mutations (13). The lack of activating TERT mutations in IDH1 mutant tumors is also corroborated by the lack of TERT mRNA and telomerase activity observed in these lesions (33).

Oligodendrogliomas.

Like astrocytomas, oligodendrogliomas often progress, and they frequently contain TERT promoter mutations (78% of 45 tumor samples) (Table S3). Oligodendroglioma was the only tumor type studied (of all types, including non-CNS tumors) (Dataset S1) in which C250T mutations were nearly as frequent as C228T mutations. In oligodendrogliomas, 43% of tumors with TERT mutations contained C250T substitutions, whereas in other gliomas, only 10% did (P<0.001, Fisher exact probability test, two-tailed). Interestingly, 91% of 45 oligodendrogliomas that were evaluated for ATRX and TERT sequence alterations contained either an ATRX coding or a TERT promoter mutation, suggesting that genetic alterations resulting in telomere maintenance are required for tumorigenesis of this subtype.

Oligodendrogliomas have long been known to contain characteristic losses of chromosome arms 1p and 19q, and these losses reflect inactivation of the CIC gene on chromosome 19q and in some cases, inactivation of the FUBP1 gene on chromosome 1p (34-36). Accordingly, 78% of 45 oligodendrogliomas contained chromosome arm 1p or 19q losses of heterozygosity (FIG. 2C) (34-36). Moreover, nearly all of them contained IDH1 or IDH2 mutations (93%).

Oligoastrocytomas.

As their name implies, these tumors are mixed, with histologic features of both oligodendrogliomas and astrocytomas. This mixture, in part, reflects the difficulties in distinguishing the various glioma subtypes from one another on the basis of histopathologic or clinical criteria (37). The genetic features of this tumor subtype reflect this mixture: the prevalence of TERT promoter mutations (25% of 24 tumors) was intermediate between oligodendrogliomas and astrocytomas, as were the frequencies of chromosome (Chr) 1p/19q losses and IDH1/2, TP53, and ATRX mutations (FIG. 2D).

Example 4—ALT Vs. TERT

ALT has been observed in tumors of the CNS (particularly gliomas) more frequently than tumors of any other tissue type. Given that TERT promoter mutations are also common in gliomas, the relationship between these two features could be determined with high confidence. The tumors depicted in FIG. 2 had previously been evaluated for alterations in ATRX, which is a nearly perfect surrogate for the ALT phenotype (11, 37). Our data show that there were 50 gliomas with ATRX mutations and 83 gliomas with TERT mutations; 0 of 83 tumors with TERT mutations contained ATRX mutations (P<0.0001, Fisher exact probability test, two-tailed).

REFERENCES

The disclosure of each reference cited is expressly incorporated herein.
1. Aubert G, Lansdorp P M. Telomeres and aging. Physiol Rev. 2008; 88(2):557-579.
2. Akiyama M, et al. Cytokines modulate telomerase activity in a human multiple myeloma cell line. Cancer Res. 2002; 62(13):3876-3882.
3. Kang S S, Kwon T, Kwon D Y, Do S I. Akt protein kinase enhances human telomerase activity through phosphorylation of telomerase reverse transcriptase subunit. J Biol Chem. 1999; 274(19):13085-13090.
4. Li H, Zhao L, Yang Z, Funder J W, Liu J P. Telomerase is controlled by protein kinase Calpha in human breast cancer cells. J Biol Chem. 1998; 273(50):33436-33442.
5. Kim N W, et al. Specific association of human telomerase activity with immortal cells and cancer. Science. 1994; 266(5193):2011-2015.
6. Shay J W, Bacchetti S. A survey of telomerase activity in human cancer. Eur J Cancer. 1997; 33(5):787-791.
7. Morrison S J, Prowse K R, Ho P, Weissman I L. Telomerase activity in hematopoietic cells is associated with self-renewal potential. Immunity. 1996; 5(3):207-216.
8. Hiyama E, Hiyama K. Telomere and telomerase in stem cells. Br J Cancer. 2007; 96(7):1020-1024.
9. Forsyth N R, Wright W E, Shay J W. Telomerase and differentiation in multicellular organisms: Turn it off, turn it on, and turn it off again. Differentiation. 2002; 69(4-5):188-197.
10. Jiao Y, et al. DAXX/ATRX, MEN1, and mTOR pathway genes are frequently altered in pancreatic neuroendocrine tumors. Science. 2011; 331(6021):1199-1203.
11. Heaphy C M, et al. Altered telomeres in tumors with ATRX and DAXX mutations. Science. 2011; 333(6041): 425.
12. Cesare A J, Reddel R R. Alternative lengthening of telomeres: Models, mechanisms and implications. Nat Rev Genet. 2010; 11(5):319-330.
13. Heaphy C M, et al. Prevalence of the alternative lengthening of telomeres telomere maintenance mechanism in human cancer subtypes. Am J Pathol. 2011; 179(4):1608-1615.
14. Horn S, et al. TERT promoter mutations in familial and sporadic melanoma. Science. 2013; 339(6122):959-961.

15. Huang F W, et al. Highly recurrent TERT promoter mutations in human melanoma. Science. 2013; 339 (6122):957-959.
16. Conyers R, Young S, Thomas D M. Liposarcoma: Molecular genetics and therapeutics. Sarcoma. 2011; 2011:483154.
17. Göransson M, et al. The myxoid liposarcoma FUS-DDIT3 fusion oncoprotein deregulates NF-kappaB target genes by interaction with NFKBIZ. Oncogene. 2009; 28(2):270-278.
18. Charytonowicz E, et al. PPARγ agonists enhance ET-743-induced adipogenic differentiation in a transgenic mouse model of myxoid round cell liposarcoma. J Clin Invest. 2012; 122(3):886-898.
19. Costa A, et al. Telomere maintenance mechanisms in liposarcomas: Association with histologic subtypes and disease progression. Cancer Res. 2006; 66(17):8918-8924.
20. Altekruse S F, McGlynn K A, Reichman M E. Hepatocellular carcinoma incidence, mortality, and survival trends in the United States from 1975 to 2005. J Clin Oncol. 2009; 27(9):1485-1491.
21. Guichard C, et al. Integrated analysis of somatic mutations and focal copy-number changes identifies key genes and pathways in hepatocellular carcinoma. Nat Genet. 2012; 44(6):694-698.
22. Li M, et al. Inactivating mutations of the chromatin remodeling gene ARID2 in hepatocellular carcinoma. Nat Genet. 2011; 43(9):828-829.
23. Siegel R, Naishadham D, Jemal A. Cancer statistics, 2013. CA Cancer J Clin. 2013; 63(1):11-30.
24. Gui Y, et al. Frequent mutations of chromatin remodeling genes in transitional cell carcinoma of the bladder. Nat Genet. 2011; 43(9):875-878.
25. Liu X, et al. HPV E6 protein interacts physically and functionally with the cellular telomerase complex. Proc Natl Acad Sci USA. 2009; 106(44):18780-18785.
26. Gilbertson R J, Ellison D W. The origins of medulloblastoma subtypes. Annu Rev Pathol. 2008; 3:341-365.
27. Adamson D C, et al. OTX2 is critical for the maintenance and progression of Shh-independent medulloblastomas. Cancer Res. 2010; 70(1):181-191.
28. Northcott P A, et al. Medulloblastoma comprises four distinct molecular variants. J Clin Oncol. 2011; 29(11):1408-1414.
29. Kool M, et al. Integrated genomics identifies five medulloblastoma subtypes with distinct genetic profiles, pathway signatures and clinicopathological features. PLoS One. 2008; 3(8):e3088.
30. Jansen M, Yip S, Louis D N. Molecular pathology in adult gliomas: Diagnostic, prognostic, and predictive markers. Lancet Neurol. 2010; 9(7):717-726.
31. Dolecek T A, Propp J M, Stroup N E, Kruchko C. CBTRUS statistical report: Primary brain and central nervous system tumors diagnosed in the United States in 2005-2009. Neuro Oncol. 2012; 14(Suppl 5):v1-v49.
32. Parsons D W, et al. An integrated genomic analysis of human glioblastoma multiforme. Science. 2008; 321 (5897): 1807-1812.
33. Boldrini L, et al. Telomerase activity and hTERT mRNA expression in glial tumors. Int J Oncol. 2006; 28(6):1555-1560.
34. Bettegowda C, et al. Mutations in CIC and FUBP1 contribute to human oligodendroglioma. Science. 2011; 333(6048):1453-1455.
35. Bromberg J E, van den Bent M J. Oligodendrogliomas: Molecular biology and treatment. Oncologist. 2009; 14(2):155-163.
36. Maintz D, et al. Molecular genetic evidence for subtypes of oligoastrocytomas. J Neuropathol Exp Neurol. 1997; 56(10):1098-1104.
37. Jiao Y, et al. Frequent ATRX, CIC, and FUBP1 mutations refine the classification of malignant gliomas. Oncotarget. 2012; 3(7):709-722.
38. King E D, Matteson J, Jacobs S C, Kyprianou N. Incidence of apoptosis, cell proliferation and bcl-2 expression in transitional cell carcinoma of the bladder: Association with tumor progression. J Urol. 1996; 155 (1):316-320.
39. Aikata H, et al. Telomere reduction in human liver tissues with age and chronic inflammation. Exp Cell Res. 2000; 256(2):578-582.
40. Spalding K L, Bhardwaj R D, Buchholz B A, Druid H, Frisén J. Retrospective birth dating of cells in humans. Cell. 2005; 122(1):133-143.
41. Cheng, et al. Bladder cancer: Translating molecular genetic insights into clinical practice. Hum Pathol. 2011; 42(4):455-481.
42. Singal A G, et al. Detection of hepatocellular carcinoma at advanced stages among patients in the HALT-C Trial: Where did surveillance fail? Am J Gastroenterol. 2012; 108(3):425-432.
43. Baraniskin A, et al. Identification of microRNAs in the cerebrospinal fluid as biomarker for the diagnosis of glioma. Neuro Oncol. 2012; 14(1):29-33.
44. Sjöblom T, et al. The consensus coding sequences of human breast and colorectal cancers. Science. 2006; 314 (5797):268-274.
45. Duncan C G, et al. Integrated genomic analyses identify ERRFI1 and TACC3 as glioblastoma-targeted genes. Oncotarget. 2010; 1(4):265-277.
46. Yan H, et al. IDH1 and IDH2 mutations in gliomas. N Engl J Med. 2009; 360(8):765-773.

The invention claimed is:

1. A method of identifying a mutation in a human subject and treating a human subject, comprising:
    subjecting a nucleic acid sample obtained from a tumor of the human selected from the group consisting of: glioma, astrocytoma, oligodendroglioma, and oligoastrocytoma, to a reaction whereby reaction products are formed;
    detecting in the reaction products from the human tumor a somatic mutation at nucleotide chr5 1,295,250 in hg19; and
    administering to the subject with the somatic mutation a therapy selected from the group consisting of chemotherapy, radiotherapy, biological therapy, or surgery.

2. The method of claim 1, wherein the tumor is a glioma.

3. The method of claim 1, wherein the tumor is an astrocytoma.

4. The method of claim 1, wherein the tumor is an oligodendroglioma.

5. The method of claim 1, wherein the tumor is an oligoastrocytoma.

6. The method of claim 1, wherein the tumor is a primary glioblastoma.

7. The method of claim 1, wherein the reaction comprises amplifying the promoter or part of the promoter of a telomerase reverse transcriptase (TERT) gene to form an amplicon.

8. The method of claim 7, wherein the amplicon is sequenced.

9. The method of claim 7, wherein the amplicon is hybridized to a mutation specific oligonucleotide.

10. The method of claim 7, wherein the reaction employs mutation-specific amplification primers.

11. The method of claim 1, wherein the reaction is a nucleic acid hybridization reaction.

12. The method of claim 11, wherein the reaction employs a mutation-specific hybridization probe.

13. The method of claim 1, wherein the reaction is a nucleic acid sequencing reaction.

14. The method of claim 1, wherein the nucleic acid sample is obtained from a primary tumor.

15. The method of claim 1, wherein prior to the step of subjecting, nucleic acids are extracted from a primary tumor sample.

16. The method of claim 1, further comprising:
subjecting a nucleic acid sample obtained from a non-tumor tissue of the human to the reaction; and
confirming that the somatic mutation detected in the tumor tissue is not in the nucleic acid sample obtained from the non-tumor tissue.

17. The method of claim 1, wherein the therapy is chemotherapy.

18. The method of claim 1, wherein the therapy is radiotherapy.

19. The method of claim 1, wherein the therapy is biological therapy.

20. The method of claim 1, wherein the therapy is surgery.

21. A method of detecting a mutation in a human subject and treating a human subject, comprising:
subjecting nucleic acid samples obtained from a plurality of tumors of a plurality of humans to a reaction to form reaction products wherein the plurality of tumors are selected from the group consisting of: glioma, astrocytoma, oligodendroglioma, and oligoastrocytoma;
detecting in the reaction products of at least one of the plurality of nucleic acid samples obtained from the plurality of tumors a somatic mutation at nucleotide chr5 1,295,250 in hg19; and
administering a therapy to at least one of the human subjects in whose tumor the somatic mutation was detected, wherein the therapy is selected from the group consisting of chemotherapy, radiotherapy, biological therapy, or surgery.

22. The method of claim 21, wherein the nucleic acid samples obtained from the plurality of tumors are obtained from primary tumors.

23. The method of claim 21, wherein prior to the step of subjecting nucleic acid samples obtained from the plurality of tumors, nucleic acids are extracted from primary tumor samples.

24. The method of claim 21, wherein the tumors are gliomas.

25. The method of claim 21, wherein the tumors are primary glioblastomas.

26. The method of claim 21, wherein the tumors are astrocytomas.

27. The method of claim 21, wherein the tumors are oligodendrogliomas.

28. The method of claim 21, wherein the tumors are oligoastrocytomas.

29. The method of claim 21, wherein the reaction comprises amplifying the promoter or part of the promoter to form an amplicon.

30. The method of claim 29, wherein the reaction employs mutation-specific amplification primers.

31. The method of claim 29, wherein the amplicon is sequenced.

32. The method of claim 29, wherein the amplicon is hybridized to a mutation specific oligonucleotide.

33. The method of claim 21, wherein the reaction is a nucleic acid hybridization reaction.

34. The method of claim 21, wherein the reaction is a nucleic acid sequencing reaction.

35. The method of claim 21, wherein the therapy is chemotherapy.

36. The method of claim 21, wherein the therapy is radiotherapy.

37. The method of claim 21, wherein the therapy is biological therapy.

38. The method of claim 21, wherein the therapy is surgery.

39. The method of claim 21, further comprising:
subjecting a plurality of nucleic acid samples obtained from a plurality of non-tumor tissues of the plurality of humans to the reaction; and
confirming that the somatic mutation detected in the tumor tissue of the at least one human subject is not present in the nucleic acid sample obtained from the non-tumor tissue of the at least one human subject.

* * * * *